US009962485B2

(12) United States Patent
Kelly et al.

(10) Patent No.: US 9,962,485 B2
(45) Date of Patent: May 8, 2018

(54) AUTOMATICALLY DISASSOCIATING MEDICAL DEVICES FROM PATIENTS

(71) Applicant: CERNER INNOVATION, INC., Kansas City, KS (US)

(72) Inventors: Lisa Kelly, Overland Park, KS (US); Judith A. Zakutny, Olathe, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 342 days.

(21) Appl. No.: 14/174,585

(22) Filed: Feb. 6, 2014

(65) Prior Publication Data

US 2015/0182696 A1 Jul. 2, 2015

Related U.S. Application Data

(60) Provisional application No. 61/921,771, filed on Dec. 30, 2013.

(51) Int. Cl.
*G06Q 50/24* (2012.01)
*A61M 5/168* (2006.01)
*G06F 19/00* (2018.01)

(52) U.S. Cl.
CPC ..... *A61M 5/16804* (2013.01); *G06F 19/3418* (2013.01); *A61M 2205/3569* (2013.01); *A61M 2205/6009* (2013.01)

(58) Field of Classification Search
CPC ..... G06F 19/322; G06F 19/327; G06Q 50/22; G06Q 50/24; G16H 10/00; G16H 10/60; G16H 40/00; G16H 40/40; G16H 40/60
USPC ........................................ 705/1.1–3; 235/375
See application file for complete search history.

(56) References Cited

U.S. PATENT DOCUMENTS

| 7,933,780 | B2 * | 4/2011 | De La Huerga .. A61M 5/14212 235/375 |
| 8,400,295 | B1 * | 3/2013 | Khaira ................... G06F 19/323 340/10.1 |
| 2004/0010425 | A1 * | 1/2004 | Wilkes et al. .................... 705/3 |
| 2005/0137653 | A1 * | 6/2005 | Friedman ............. A61B 5/0002 607/60 |

(Continued)

OTHER PUBLICATIONS

Identification of Barriers and Enablers for Device Interoperability—Provider Panel, HIT Standards Committee Clinical Operations Workgroup Mar. 28, 2011, Washington DC, 3 pages.*

*Primary Examiner* — Jason S Tiedeman
(74) *Attorney, Agent, or Firm* — Shook, Hardy & Bacon L.L.P.

(57) ABSTRACT

Systems, methods, computer storage media, and user interfaces are provided for automatically disassociating medical devices from patients. An indication that a medical device is associated with a patient and is online is received. A disruption in the communication with the medical device that has not been disassociated with the patient is identified. In embodiments, the disruption indicates the medical device has lost a wireless connection, is associated with a scheduled downtime, has been powered off, or is offline. Once it is determined that a predetermined period of time has elapsed since the disruption, the medical device is automatically disassociated from the patient. In embodiments, the medical device is retroactively re-associated to the patient if it is determined the medical device should not have been automatically disassociated from the patient.

16 Claims, 3 Drawing Sheets

(56) References Cited

U.S. PATENT DOCUMENTS

| | | | |
|---|---|---|---|
| 2005/0209886 A1* | 9/2005 | Corkern | G06Q 50/22 705/2 |
| 2006/0064020 A1* | 3/2006 | Burnes | G06F 19/3418 600/481 |
| 2008/0108884 A1* | 5/2008 | Kiani | A61B 5/0002 600/301 |
| 2009/0099867 A1* | 4/2009 | Newman | G06F 19/327 705/2 |
| 2009/0112630 A1* | 4/2009 | Collins, Jr. | G06F 19/327 705/3 |
| 2009/0231124 A1* | 9/2009 | Klabunde | A61B 5/0205 340/539.12 |
| 2010/0169120 A1* | 7/2010 | Herbst et al. | 705/3 |
| 2010/0179819 A1* | 7/2010 | Herbst | G06Q 10/10 705/2 |
| 2010/0287006 A1* | 11/2010 | Cannon | G06F 19/327 705/3 |
| 2011/0071844 A1* | 3/2011 | Cannon | A61M 5/172 705/2 |
| 2012/0323592 A1* | 12/2012 | Bechtel | G06F 19/3406 705/2 |
| 2013/0092728 A1* | 4/2013 | Vik | G06Q 50/22 235/375 |
| 2013/0127620 A1* | 5/2013 | Siebers | G08B 21/02 340/573.1 |
| 2013/0267475 A1* | 10/2013 | Addington | A61K 31/704 514/26 |
| 2013/0321145 A1* | 12/2013 | Ranieri | G06F 19/327 340/539.12 |
| 2014/0142963 A1* | 5/2014 | Hill | G06F 19/322 705/2 |
| 2014/0171753 A1* | 6/2014 | Montejo | A61B 5/0022 600/301 |
| 2014/0195446 A1* | 7/2014 | Yurach | G06Q 30/018 705/317 |
| 2014/0266713 A1* | 9/2014 | Sehgal | G08B 23/00 340/540 |

* cited by examiner

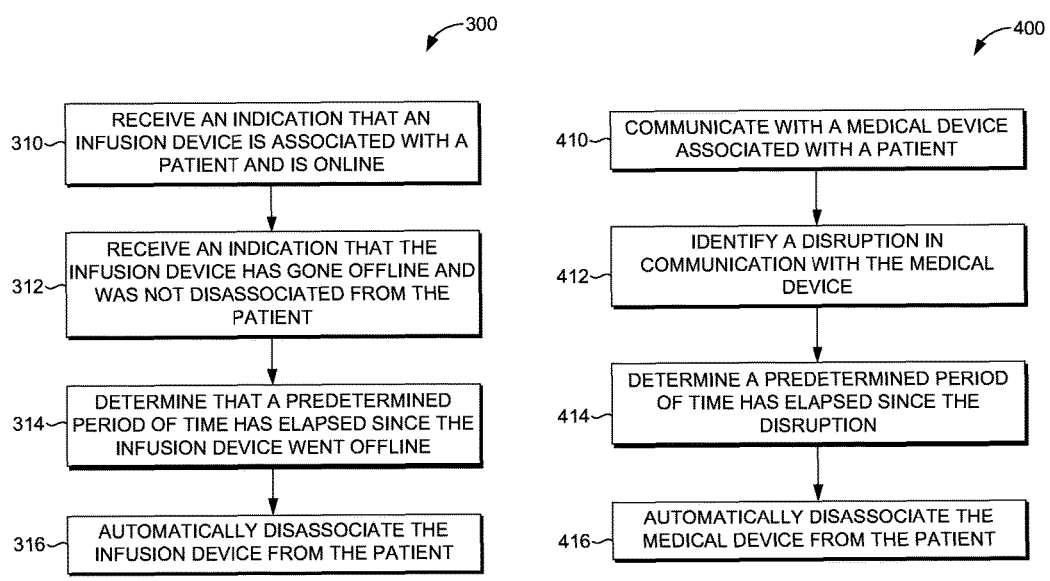

AUTOMATICALLY DISASSOCIATING MEDICAL DEVICES FROM PATIENTS

CROSS-REFERENCE TO RELATED APPLICATIONS

This application claims priority to U.S. Provisional Application Ser. No. 61/921,771, filed Dec. 30, 2013, entitled "AUTOMATICALLY DISASSOCIATING MEDICAL DEVICES FROM PATIENTS," which is incorporated herein by reference in its entirety.

BACKGROUND

Typically, medical devices that are used to treat or care for a patient are not adequately or timely linked to that patient in the patient's record, such as an electronic medical record (EMR). In many instances, these errors in linkage or association may lead to inaccuracies and inconsistencies in treating the patient. Even when the devices are properly linked or associated with a patient, the manual process required to unlink or disassociate a device from a patient is often overlooked or forgotten. Data that should be attributed to a new patient utilizing the device remains attributed to the previous patient. This lack of properly and timely disassociating the device results in many inaccuracies and inconsistencies in treating both patients.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Embodiments of the present invention provide systems, methods, computer storage media for automatically disassociating medical devices from patients. An indication that a medical device is associated with a patient and is online is received. In embodiments, the medical device is one or more of: an infusion device, a balloon pump, a ventilator, a dialysis machine, a cardiac output machine, a patient-controlled analgesia (PCA) pump, or a patient-controlled epidural analgesia (PCEA) pump. A disruption in the communication with the medical device that has not been disassociated from the patient is identified. In embodiments, the disruption indicates the medical device has lost a wireless connection, is associated with a scheduled downtime, has been powered off, or is offline. Once it is determined that a predetermined period of time has elapsed since the disruption, the medical device is automatically disassociated from the patient. In embodiments, the medical device is retroactively re-associated to the patient if it is determined the medical device should not have been automatically disassociated from the patient.

BRIEF DESCRIPTION OF THE DRAWINGS

Embodiments are described in detail below with reference to the attached drawing figures, wherein:

FIG. 3 is an illustrative flow diagram of a method for automatically disassociating medical devices from patients, in accordance with an embodiment of the present invention; and FIG. 4 is an illustrative flow diagram of a method for automatically disassociating medical devices from patients, in accordance with an embodiment of the present invention.

DETAILED DESCRIPTION

Figure 1:
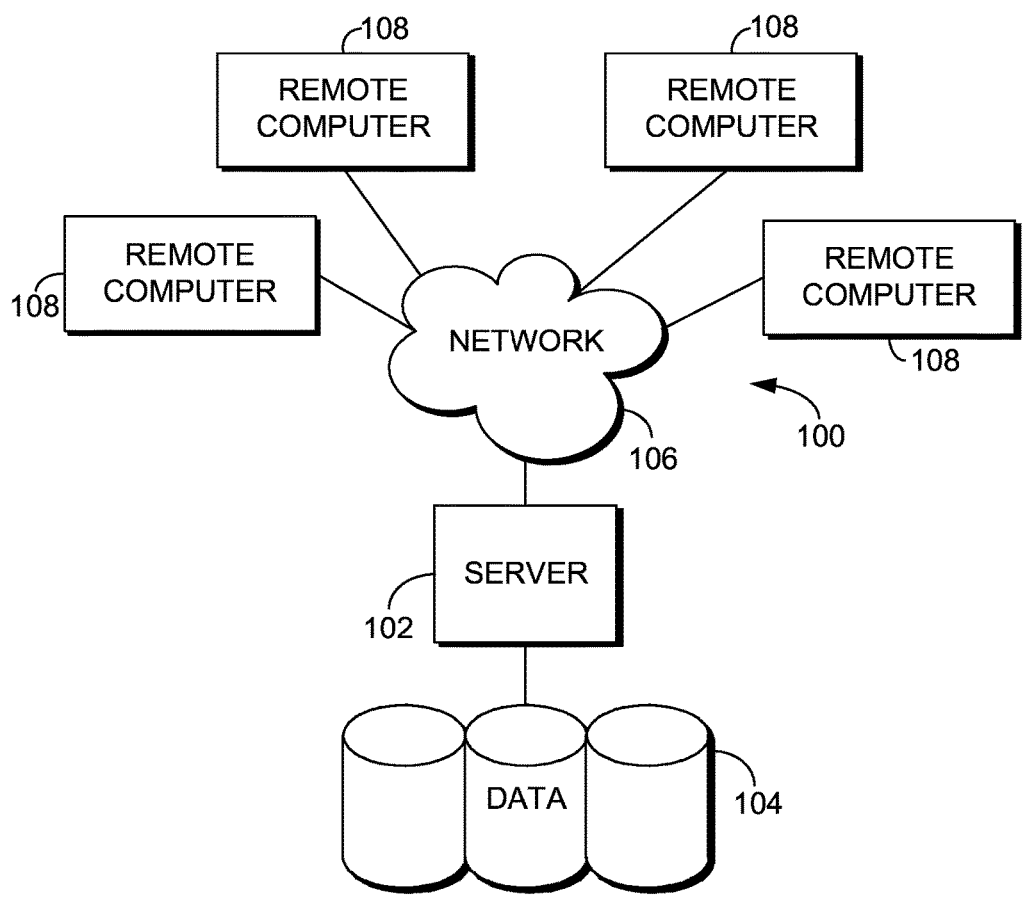
FIG. 1 is a block diagram of an exemplary computing environment suitable for use in implementing embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide systems, methods, computer storage media, and user interfaces for, among other things, automatically disassociating medical devices from patients. An indication that a medical device is associated with a patient and is online is received. In embodiments, the medical device is one or more of: an infusion device, a balloon pump, a ventilator, a dialysis machine, a cardiac output machine, a PCA pump, or a PCEA pump. A disruption in the communication with the medical device that has not been disassociated with the patient is identified. In embodiments, the disruption indicates the medical device has lost a wireless connection, is associated with a scheduled downtime, has been powered off, or is offline. Once it is determined that a predetermined period of time has elapsed since the disruption, the medical device is automatically disassociated from the patient. In embodiments, the medical device is retroactively re-associated to the patient if it is determined the medical device should not have been automatically disassociated from the patient.

In various embodiments of the present invention, data from a medical device may be communicated to a patient's EMR while the patient is associated with the medical device. As utilized herein, the acronym "EMR" is not meant to be limiting, and may broadly refer to any or all aspects of the patient's medical record rendered in a digital format. Generally, the EMR is supported by systems configured to co-ordinate the storage and retrieval of individual records with the aid of computing devices. As such, a variety of types of healthcare-related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); evidence-based recommendations for specific medical conditions; a record of appointments and physician's notes; billing records; and data received from an associated medical device. Accordingly, systems that employ EMRs reduce medical errors, increase physician efficiency, and reduce costs, as well as promote standardization of healthcare.

Accordingly, one embodiment of the present invention is directed to one or more computer storage media storing computer-useable instructions that, when used by one or more computing devices, cause the one or more computing devices to perform a method for automatically disassociating an infusion device from a patient. The method comprises: receiving an indication that an infusion device is associated with a patient and is online; receiving an indication that the infusion device has gone offline and was not disassociated form the patient; determining that a predetermined period of time has elapsed since the infusion device went offline; and automatically disassociating the infusion device.

In another embodiment, the present invention is directed to a system for automatically disassociating a medical device from a patient. The system comprises one or more processors coupled to a computer hardware storage medium, the computer hardware storage medium having stored thereon a plurality of computer software components executable by the one or more processors. The computer software components comprise: an association component that receives an indication that a medical device is associated with a patient and is online; an offline component that receives an indication that the medical device has gone offline and was not disassociated from the patient; an elapsed time component that receives an indication that a predetermined period of time has elapsed since the medical device went offline; and a disassociation component that automatically disassociates the medical device.

In yet another embodiment, the present invention is directed to a method for automatically disassociating a medical device from a patient. The method comprises: receiving a communication from a medical device associated with a patient; identifying a disruption in communication with the medical device, the medical device not being disassociated from the patient, wherein the disruption indicates the medical device has lost a wireless connection, is associated with a scheduled downtime, has been powered off, or is offline; determining a predetermined period of time has elapsed since the disruption; and automatically disassociating the medical device from the patient.

Having briefly described embodiments of the present invention, an exemplary operating environment suitable for use in implementing embodiments of the present invention is described below. Referring to the drawings in general, and initially to FIG. 1 in particular, an exemplary computing system environment, for instance, a medical information computing system environment, with which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 100 includes a general purpose computing device in the form of a control server 102. Components of the control server 102 may include, without limitation, a processing unit, internal system memory, and a suitable system bus for coupling various system components, including database cluster 104, with the control server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media, for instance, database cluster 104. Computer-readable media can be any available media that may be accessed by server 102, and includes volatile and nonvolatile media, as well as removable and non-removable media. By way of example, and not limitation, computer-readable media may include computer storage media and communication media; computer storage media excluding signals per se. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. The control server 102 may operate in a computer network 106 using logical connections to one or more remote computers 108. Remote computers 108 may be located at a variety of locations in a medical or research environment, for example, but not limited to, clinical laboratories (e.g., molecular diagnostic laboratories), hospitals and other inpatient settings, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the elements described above in relation to the control server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the control server 102 may include a modem or other means for establishing communications via the WAN, such as the Internet. In a networked environment, program modules or portions thereof may be stored in association with the control server 102, the database cluster 104, or any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) may be utilized.

In operation, a clinician may enter commands and information into the control server 102 or convey the commands and information to the control server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 102. In addition to a monitor, the control server 102 and/or remote computers 108 may include other peripheral output devices, such as speakers and a printer.

Although many other internal components of the control server 102 and the remote computers 108 are not shown, those of ordinary skill in the art will appreciate that such components and their interconnection are well known. Accordingly, additional details concerning the internal construction of the control server 102 and the remote computers 108 are not further disclosed herein.

As previously mentioned, embodiments of the present invention provide systems, methods, computer storage media, and user interfaces for automatically disassociating medical devices from patients. An indication that a medical device is associated with a patient and is online is received. In embodiments, the medical device is one or more of: an infusion device, a balloon pump, a ventilator, a dialysis machine, a cardiac output machine, a PCA pump, or a PCEA pump. A disruption in the communication with the medical device that has not been disassociated with the patient is identified. In embodiments, the disruption indicates the medical device has lost a wireless connection, is associated with a scheduled downtime, has been powered off, or is offline. Once it is determined that a predetermined period of time has elapsed since the disruption, the medical device is automatically disassociated from the patient. In embodiments, the medical device is retroactively re-associated to the patient if it is determined the medical device should not have been automatically disassociated from the patient.

Figure 2:
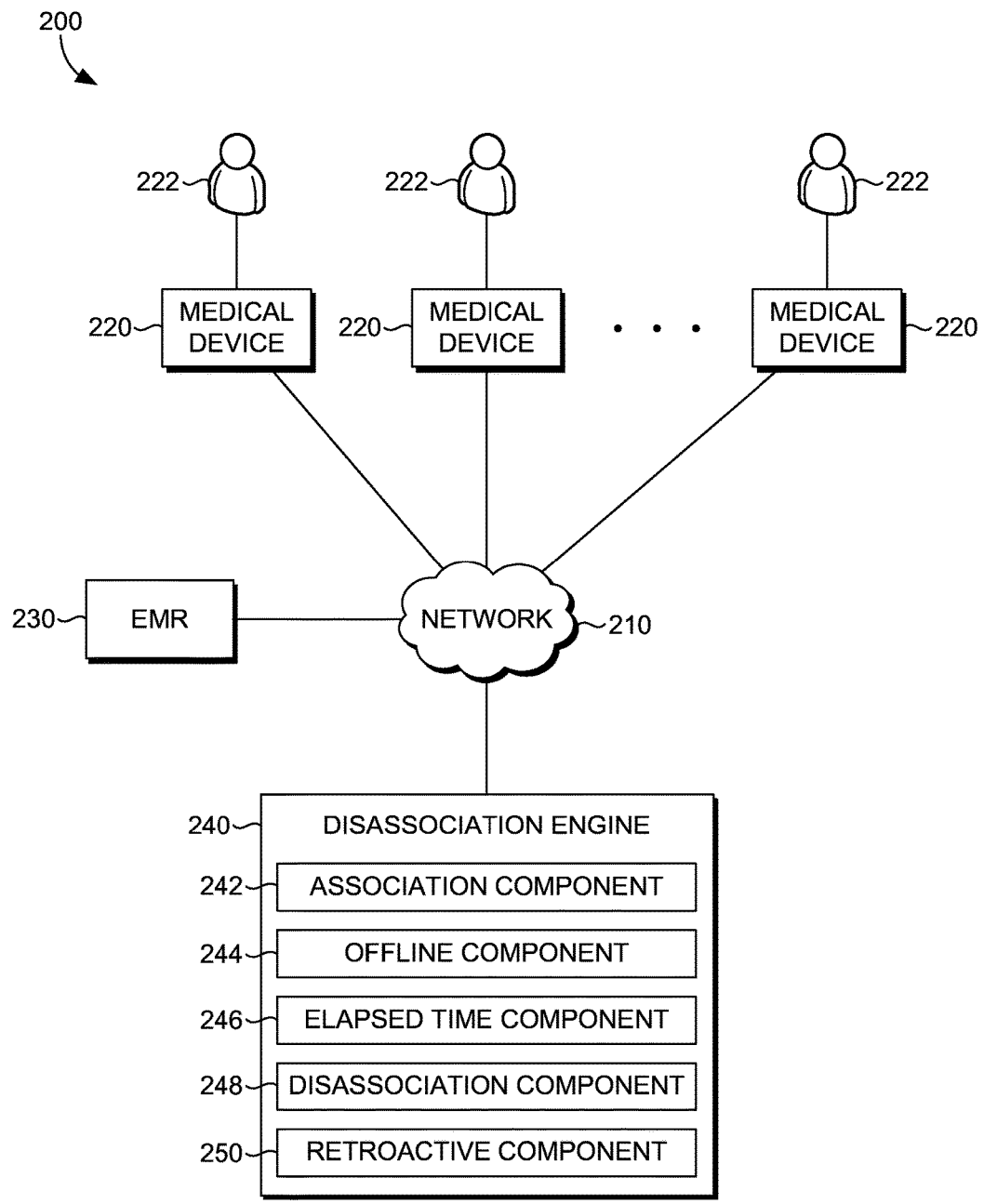
FIG. 2 is an exemplary system architecture suitable for use in implementing embodiments of the present invention.

Referring now to FIG. 2, a block diagram is provided illustrating an exemplary computing system 200 suitable for use in implementing embodiments of the present invention. Generally, the computing system 200 allows for communication via a network 210 between medical devices 220, an EMR 230, and a disassociation engine 240. The functionality provided by disassociation engine 240 may be distributed across one or more of the medical devices 220, or may be provided by a standalone computing device, such as server 102 as illustrated in FIG. 1. Medical devices may include any medical device that could be used to treat a patient, or any devices or mechanisms that may be used by a patient during a hospital stay or doctor's office visit, for example. These medical devices may include, for exemplary purposes only, a patient's bed, monitors (e.g., fetal monitors), pumps (e.g., balloon pumps, infusion pumps), cardiac output machines, ventilators, sequential compression devices, electronic security devices, a dialysis machine, a PCA pump, a PCEA pump, and the like.

Each of medical devices 220, the EMR 230, and the disassociation engine 240 may communicate via the network 210 utilizing the same or different communication protocols. The network 210 may include, without limitation, one or more local area networks (LANs), one or more wide area networks (WANs), and/or one or more personal area networks (PANs).

It should be understood that any number or type of medical devices 220 and/or disassociation engines 240 may be employed in the computing system 200 within the scope of embodiments of the present invention. Each may comprise a single device/interface or multiple devices/interfaces cooperating in a distributed environment. For instance, the disassociation engine 240 may comprise multiple devices and/or modules arranged in a distributed environment that collectively provide the functionality of the disassociation engine 240 described herein. Additionally, other components or modules not shown also may be included within the computing system 200.

In some embodiments, one or more of the illustrated components/modules may be implemented as stand-alone applications. In other embodiments, one or more of the illustrated components/modules may be implemented via medical devices 220, disassociation engine 240, or as an Internet-based service. It will be understood by those of ordinary skill in the art that the components/modules illustrated in FIG. 2 are exemplary in nature and in number and should not be construed as limiting. Any number of components/modules may be employed to achieve the desired functionality within the scope of embodiments hereof. Further, components/modules may be located on and/or shared by any number of disassociation engine 240 and/or medical devices 220. By way of example only, the disassociation engine 240 might be provided as a single computing device (as shown), a cluster of computing devices, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Referring still to FIG. 2, the disassociation engine 240 is configured to, among other things, automatically disassociate medical devices from patients. The disassociation engine 240 is additionally configured to, among other things, retroactively re-associate medical devices to patients. As illustrated, in various embodiments, the disassociation engine 240 includes an association component 242, an offline component 244, an elapsed time component 246, a disassociation component 248, and a retroactive component 250.

Association component 242 receives an indication that a medical device 220 is associated with a patient 222 and is online. This association enables data from medical devices 220 to be communicated to an EMR associated with each patient 222. The EMR 230 is configured to receive device information communicated by the one or more medical devices 220. The medical devices 220 may communicate with the EMR 230 via any of the communication protocols described herein.

Offline component 244 receives an indication that the medical device has gone offline and was not disassociated from the patient. The device being offline may indicate that the medical device is no longer able to communicate with the network 210, the EMR 230, and/or the disassociation engine 240. For example, a wireless connection associated with the medical device may have been lost causing the medical device to go offline. In another example, a schedule downtime may have occurred causing the medical device to go offline. In yet another example, the medical device may have been powered off causing it to go offline. In each of these examples, the medical device is not in a standby or paused mode; rather, it is offline and unable to communicate with the network 210, the EMR 230, and/or the disassociation engine 240 and may be unable to receive any data associated with the patient 222.

Elapsed time component 246 receives an indication that a predetermined period of time has elapsed since the medical device went offline. The predetermined period of time may be configurable by a healthcare facility or clinician. The predetermined period of time may be based on a preference of the healthcare facility, a unit of the healthcare facility, an individual clinician, a type of patient, a diagnosis associated with the patient, and the like.

Disassociation component 248 automatically disassociates the medical device from the patient once the elapsed time component 246 receives the indication that the predetermined period of time has elapsed. In one embodiment, the disassociation component 248 further receives additional information associated with a device location, a patient location, or an order associated with the medical device. Such additional information may be further utilized to determine if the medical device should be disassociated from the patient. For example, if the predetermined period of time has elapsed, disassociation component 248 may determine the medical device should be disassociated from the patient. In one embodiment, this determination may be made prior to the predetermined period of time elapsing based on the additional information.

In one embodiment, retroactive component 250 determines the medical device should not be automatically disassociated based on the additional information. For example, even after the predetermined period of time has elapsed, the retroactive component 250 may determine the medical device should still be associated to the patient (e.g., based on an interaction by a clinician). Similarly, the retroactive component 250 may determine the medical device is still operating (i.e., the device is not offline but has a scheduled downtime associated with it or has lost wireless communication). For example, an infusing pump may still be infusing even though it had a scheduled downtime or lost a wireless signal. In these examples, the retroactive component 250 automatically retroactively re-associates the automatically disassociated medical device to the patient. In one embodiment, the retroactive component 250 further re-associates an order to the automatically disassociated medical device.

In practice, a medical device may be running and associated to a patient. The medical device may be turned off and also offline (e.g., not communicating), but not disassociated from the patient. A wireless connection may be lost or a scheduled downtime may occur. After a predetermined period of time (e.g., the time required to clean the device), the device is automatically disassociated from the patient before being used for the new patient. This prevents data that should be associated with the new patient from being associated with the previous patient.

In another example, the medical device may be turned off and offline, but not disassociated from the patient. If the medical device remains at the bedside and a predetermined period of time has elapsed since the medical device went offline, the medical device is disassociated from the patient.

Turning to FIG. 3, an illustrative flow diagram 300 is shown of a method for automatically disassociating a medical device from a patient, in accordance with an embodiment of the present invention. Initially, at step 310, an indication that an infusion device is associated with a patient and is online is received. An indication that the infusion device has gone offline and was not disassociated from the patient is received at step 312. In one embodiment, the infusion device is not in a standby or paused mode. It is determined, at step 314, that a predetermined period of time has elapsed since the infusion device went offline. At step, 316, the infusion device is automatically disassociated from the patient.

In one embodiment, a wireless connection associated with the infusion device has been lost causing the infusion device to go offline. In one embodiment, a scheduled downtime has occurred causing the infusion device to go offline. In one embodiment, the infusion device has been powered off causing it to go offline.

In one embodiment, an indication to retroactively re-associate an automatically disassociated infusion device to the patient is received. For example, if it is determined the infusion device should not have been disassociated from the patient, the infusion device can be retroactively re-associated to the patient to prevent any gaps in data that may be communicated to the EMR associated with the patient. In one embodiment, an indication to re-associate an order to the automatically disassociated infusion device is received.

Turning to FIG. 4, an illustrative flow diagram 400 is shown of a method for automatically disassociating a medical device from a patient, in accordance with an embodiment of the present invention. Initially, at step 410, a communication is received from a medical device associated with a patient. In embodiments, the medical device is one or more of: an infusion device, a balloon pump, a ventilator, a dialysis machine, a cardiac output machine, a PCA pump, or a PCEA pump. The communication may be data associated with the medical device. The communication may be an indication that the medical device is online (e.g., a heartbeat signal).

At step 412, a disruption in communication with the medical device that has not been disassociated from the patient is identified. In embodiments, the disruption indicates the medical device has lost a wireless connection, is associated with a scheduled downtime, has been powered off, or is offline. However, the medical device is not in a standby or paused mode. Rather, it is offline and unable to communicate with the network, the EMR, or the disassociation engine.

A predetermined period of time is determined to have elapsed since the disruption, at step 414. The predetermined period of time may be configurable based on a preference of the healthcare facility, a unit of the healthcare facility, an individual clinician, a type of patient, a diagnosis associated with the patient, and the like.

At step 416, the medical device is automatically disassociated from the patient. For clarity, a clinician does not have to manually disassociate the medical device from the patient. Instead, as soon as the predetermined period of time elapses since the disruption, the medical device is no longer associated with the patient.

In one embodiment, it is determined that the medical device should not have been automatically disassociated from the patient. The medical device may be retroactively re-associated to the patient.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. One or more non-transitory computer storage media having computer-executable instructions embodied thereon that, when executed by one or more computing devices, cause the one or more computing devices to perform a method, the method comprising:
receiving an association of a wireless infusion device with a first patient, wherein the association indicates that infusion data outputted by the wireless infusion device, when providing infusion services to the first patient, is stored in an electronic medical record of the first patient;
receiving an indication that the wireless infusion device that is associated with the first patient is online and an indication that the wireless infusion device is providing infusion services to the first patient,
wherein the wireless infusion device is indicated to be online when a wireless connection is maintained between the wireless infusion device and the one or more computing devices via a network, and
wherein the wireless infusion device is indicated to be providing infusion services to the first patient when the infusion data outputted by the wireless infusion device associated with the first patient is received by the one or more computing devices via the network;
storing the infusion data in the electronic medical record of the associated first patient;
receiving an indication that the wireless infusion device has gone offline and was not disassociated from the first patient after going offline, wherein the wireless infusion device is indicated as offline when the wireless infusion device is no longer determined to be wirelessly connected to the one or more computing devices via the network;
storing additional infusion data output by the wireless infusion device associated with the first patient as offline data at the wireless infusion device when the additional infusion data is output while the wireless infusion device is indicated as offline;
accessing a predetermined disassociation period of time;
determining that the predetermined disassociation period of time has elapsed since the wireless infusion device went offline;
receiving location information indicating a location of the wireless infusion device and a location of the first patient associated with the wireless infusion device;
accessing a predetermined location difference threshold;
automatically disassociating the wireless infusion device from the first patient when it is determined that the predetermined disassociation period of time has elapsed since the wireless infusion device went offline and the location of wireless infusion device does not correspond to the location of the first patient by comparing the location of the first patient and the location of the wireless infusion device to the predetermined location difference threshold and determining if the threshold is met or exceeded; and
receiving a first subsequent indication that the disassociated wireless infusion device is still providing infusion services to the first patient and is online;
upon receiving the first subsequent indication, automatically re-associating the disassociated wireless infusion device with the first patient and transmitting the stored offline data and any new infusion data received after re-association to the electronic medical record of the first patient to prevent gaps in communication of data output from the disassociated wireless infusion device to the electronic medical record of the first patient;
after automatically re-associating the wireless infusion device with the first patient, receiving a second subsequent association indicating that the wireless infusion device is providing infusion services to a second patient;
disassociating the wireless infusion device from the first patient in order to prevent any subsequently output infusion data from the wireless infusion device providing infusion services to the second patient from being stored in the electronic medical record of the first patient that was previously associated with the wireless infusion device; and associating the wireless infusion device with the second patient, wherein the association of the wireless infusion device with the second patient causes the wireless infusion device providing infusion services to the second patient, when wirelessly connected to the network, to store the subsequently output infusion data in an electronic medical record associated with the second patient.

2. The media of claim 1, wherein a scheduled downtime has occurred causing the wireless infusion device to go offline.

3. The media of claim 1, wherein the wireless infusion device is not in a standby or paused mode.

4. The media of claim 1, wherein the predetermined disassociation period of time is configurable by a healthcare facility or clinician.

5. The media of claim 1, wherein the predetermined disassociation period of time is based on a preference of a healthcare facility, a unit of the healthcare facility, an individual clinician, a type of patient, or a diagnosis associated with the first patient.

6. The media of claim 1 having computer-executable instructions embodied thereon that, when executed by one or more computing devices, cause the one or more computing devices to perform a method, the method further comprising:

based on the automatic disassociation of the wireless infusion device from the first patient, disassociating the wireless infusion device from a medical order.

7. The media of claim 6 having computer-executable instructions embodied thereon that, when executed by one or more computing devices, cause the one or more computing devices to perform a method, the method further comprising:

based on the automatic re-association of the disassociated wireless infusion device with the first patient, re-associating the wireless infusion device with the medical order.

8. The media of claim 1, wherein the predetermined disassociation period of time is an amount of time specified for cleaning the wireless infusion device between different patients.

9. The media of claim 1 having computer-executable instructions embodied thereon that, when executed by one or more computing devices, cause the one or more computing devices to perform a method, the method further comprising:

determining that, when the wireless infusion device is no longer determined to be wirelessly connected to the one or more computing devices via the network and has gone offline, the wireless infusion device is associated with a scheduled downtime.

10. The media of claim 1, wherein when the wireless infusion device has gone offline, the wireless infusion device is not in a paused mode or a standby mode.

11. A system for automatically disassociating a medical device from a patient, a computer system including one or more processors coupled to a computer hardware storage medium, the computer hardware storage medium having stored thereon a plurality of computer software components executable by the one or more processors, the computer software components comprising:

an association component that:

receives an association of a wireless medical device with a first patient, wherein the association indicates that medical monitoring information outputted by the wireless medical device, when providing monitoring services to the first patient, is stored in an electronic medical record of the first patient;

receives an indication that the wireless medical device associated with the first patient is monitoring the first patient and is online, wherein the wireless medical device is indicated to be online when a wireless connection is maintained between the wireless medical device and the one or more computing devices via a network, and wherein the wireless medical device is indicated to be providing monitoring services to the first patient when the medical monitoring information corresponding to the first patient is received from the wireless medical device by the one or more computing devices via the network;

a storage component that stores the medical monitoring information to the electronic medical record of the associated first patient;

an offline component that:

receives an indication that the wireless medical device has gone offline and was not disassociated from the first patient after going offline, wherein the wireless medical device is indicated as offline when the wireless medical device is no longer determined to be wirelessly connected to the network, wherein any additional medical monitoring information collected when the wireless medical device is stored offline as offline data at the wireless medical device;

an elapsed time component that accesses a predetermined disassociation period of time and determines that the predetermined disassociation period of time has elapsed since the wireless medical device has gone offline;

a disassociation component that:

receives location information indicating a location of the wireless medical device and a location of the first patient associated with the wireless medical device;

accesses a predetermined location difference threshold;

receives a notice of the indication from the elapsed time component; and automatically disassociates the wireless medical device from the first patient when the predetermined location difference threshold is met or exceeded and the predetermined disassociation period of time has elapsed since the wireless medical device has gone offline, wherein automatic disassociation of the wireless medical device prevents any new medical monitoring information from the wireless medical device from being stored in the electronic record of the first patient; and a retroactive component that:

receives a first subsequent indication that the disassociated wireless medical device is still monitoring the first patient and is online;

upon receipt of the first subsequent indication, automatically re-associates the disassociated wireless medical device with the first patient based on the first subsequent indication that the wireless medical device is still monitoring the patient and causes the wireless medical device to transmit the stored offline data and the new medical monitoring information received after re-association to the electronic medical record of the first patient in order to prevent gaps in communication of data from the wireless medical device to the electronic medical record associated with the first patient when the wireless medical device resumes being wirelessly connected to the network;

after automatic re-association of the disassociated wireless medical device with the first patient, receives a second subsequent association indicating that the wireless medical device is providing monitoring services to a second patient;

disassociates the wireless medical device from the first patient in order to prevent subsequently output medical monitoring information from the wireless medical device providing monitoring services to the second patient from being associated with the electronic medical record of the first patient that was previously associated with the wireless medical device; and associates the wireless medical device with the second patient, wherein the association of the wireless medical device with the second patient to communicate the subsequently output medical monitoring information, when wirelessly connected to the network, to an electronic medical record associated with the second patient.

12. The system of claim 11, wherein the predetermined disassociation period of time is configurable based on at least one of a unit of a healthcare facility, a type of patient, or a diagnosis associated with the first patient.

13. The system of claim 11, wherein the indication that the wireless medical device associated with the first patient is monitoring the first patient and is online is communicated by a clinician.

14. A computer-implemented method comprising:

receiving a wireless communication of collected medical data, via a network, from a medical device associated with a first patient and that is operating and collecting the medical data with regards to the first patient, wherein operating and collecting the medical data with regards to the first patient comprises monitoring the first patient or providing infusion services to the first patient and collecting the medical data of the monitoring or infusion services, wherein the association of the medical device with the first patient causes the medical device that is wirelessly connected to the network to communicate the collected medical data to an electronic record associated with the first patient;

identifying a disruption in the wireless communication of the collected medical data from the medical device that indicates the medical device lost a wireless connection to the network and is thus offline;

storing additional medical data collected when the medical device is offline as offline data at the medical device;

accessing a predetermined disassociation period of time;

receiving location information indicating a location of the wireless infusion device and a location of the first patient associated with the medical device;

accessing a predetermined location difference threshold;

identifying that the medical device remains associated with the first patient after the disruption is identified;

determining the predetermined disassociation period of time has elapsed since the disruption;

upon determining the predetermined disassociation period of time has elapsed since the disruption and the location of the medical device does not correspond to a location of the first patient associated with the medical device by comparing the location of the first patient and the location of the medical device to the predetermined location difference threshold and determining if the threshold is met or exceeded, automatically disassociating the medical device from the first patient in order to prevent any new collected medical data from the medical device and presumed to regard another patient from being associated with the electronic record of the first patient;

when a first subsequent indication is received from the disassociated medical device that the disassociated medical device is still in operation with regard to the first patient, automatically re-associating the disassociated medical device with the first patient and transmitting the stored offline data and the new collected medical data received after re-association to the electronic medical record of the first patient in order to prevent gaps in communication of data from the medical device to the electronic record associated with the first patient;

after automatically re-associating the disassociated medical device with the first patient, receiving a second subsequent association indicating that the medical device is providing monitoring or infusion services to a second patient;

disassociating the medical device from the first patient in order to prevent subsequently collected medical data from the medical device providing monitoring or infusion services to the second patient from being associated with the electronic medical record of the first patient that was previously associated with the medical device; and associating the medical device with the second patient, wherein the association of the medical device with the second patient causes the medical device providing monitoring or infusion services to the second patient to communicate the subsequently collected medical data, when wirelessly connected to the network, to an electronic medical record associated with the second patient.

15. The method of claim 14, wherein the medical device is not in a standby or paused mode.

16. The method of claim 14, wherein the medical device is one or more of: an infusion device, a balloon pump, a ventilator, a dialysis machine, a cardiac output machine, a patient-controlled analgesia (PCA) pump, or a patient-controlled epidural analgesia (PCEA) pump.

* * * * *